(12) United States Patent
Landman et al.

(10) Patent No.: US 7,766,987 B2
(45) Date of Patent: Aug. 3, 2010

(54) APPARATUS AND METHOD FOR COLLECTION OF PARTICULATE MATTER DURING PERCUTANEOUS PROCEDURES

(75) Inventors: Jaime Landman, New York, NY (US); Walter N. Ryan, Columbus, IN (US)

(73) Assignee: Vance Products Incorporated, Spencer (IN)

( * ) Notice: Subject to any disclaimer, the term of this patent is extended or adjusted under 35 U.S.C. 154(b) by 599 days.

(21) Appl. No.: 11/738,945

(22) Filed: Apr. 23, 2007

(65) Prior Publication Data

US 2007/0245699 A1   Oct. 25, 2007

Related U.S. Application Data (60) Provisional application No. 60/794,750, filed on Apr. 25, 2006.

(51) Int. Cl.
- *A61M 5/00* (2006.01)
- *A61M 5/32* (2006.01)
- *A61M 25/00* (2006.01)

(52) U.S. Cl. ............... 55/385.1; 604/38; 604/45; 604/102.02; 604/102.03; 604/190; 604/236; 604/237; 604/517

(58) Field of Classification Search ............... 55/385.1; 604/45, 517, 102.02, 102.03, 38, 190, 236, 604/237

See application file for complete search history.

(56) References Cited

U.S. PATENT DOCUMENTS

| 4,221,225 A | | 9/1980 | Sloan |
| 4,332,250 A | * | 6/1982 | Behney ............ 604/517 |
| 4,573,965 A | * | 3/1986 | Russo ............. 604/30 |
| 5,232,443 A | * | 8/1993 | Leach ............ 604/517 |
| 5,295,979 A | | 3/1994 | DeLaurentis et al. |
| 5,338,294 A | | 8/1994 | Blake |
| 5,382,229 A | | 1/1995 | Grabenkort et al. |
| 6,004,290 A | * | 12/1999 | Davis ............ 604/103.03 |

OTHER PUBLICATIONS

International Preliminary Report on Patentability, dated Nov. 6, 2008, related application PCT/US2007/009728.
International Search Report and Written Opinion for related PCT application PCT/US2007/009723 dated Oct. 4, 2007.

\* cited by examiner

*Primary Examiner*—Duane Smith
*Assistant Examiner*—Minh-Chau T Pham
(74) *Attorney, Agent, or Firm*—Brinks Hofer Gilson & Lione (57) ABSTRACT

An apparatus and method used in a urological procedure. The apparatus includes a sheath capable of insertion into a passageway within a patient. A filter is provided that includes a mesh that retains any particulate matter that is entrained with the liquid and allows the liquid to pass therethrough. The filter may be removeably attached to receive flow from an outlet of the sheath.

13 Claims, 8 Drawing Sheets

APPARATUS AND METHOD FOR COLLECTION OF PARTICULATE MATTER DURING PERCUTANEOUS PROCEDURES

CROSS-REFERENCE TO RELATED APPLICATIONS

This application claims priority to U.S. Provisional Application No. 60/794,750, filed on Apr. 25, 2006, and is hereby fully incorporated by reference herein.

FIELD OF THE INVENTION

The present invention relates to urology and specifically to devices and apparatus for use with percutaneous urological procedures.

BACKGROUND OF THE INVENTION

In the past many urological procedures were performed percutaneously, which created many problems and added extra steps and side effects to the procedure. For example, percutaneous procedures were performed on the kidney, such as percutaneous nephrolithotomy for staghorn or partial staghorn renal calculi. A significant amount of irrigant is often used during these procedures, which may wash particulate down the ureter. The particulate matter within the irrigant has been known to cause blockage within the urinary tract when it is allowed to flow through this flow path during these types of procedures. Because the ureter is formed with a relatively small cross-sectional area, it is a known problem that particulate matter from the kidney can become lodged within the ureter or the junctions between the kidney and the ureter, and between the ureter, the bladder, and the ureteral-vesico junction (UVJ). This type of blockage can have harmful effects on the patient, such as discomfort, hyrdonephrosis, and infection, and must be treated to allow the urinary system to function properly.

Therefore, it is common to employ a balloon at the ureteropelvic junction (UPJ). The balloon occludes the urinary tract downstream of the kidney and avoids the problem of particulate matter being entrained within the irrigant and becoming lodged within the urinary tract. While this step is often successful in preventing the blockage of the downstream urinary tract, it has been shown to increase renal pressure, which can result in post operative complications.

To avoid these problems, and the additional general problems that come with any percutaneous procedure, the use of flexible, kink-resistant introducer sheaths have been employed to perform urological procedures. These sheaths may be introduced into the urinary tract through the urethral meatus and extend through the urethra, the bladder, and the ureter to reach the UPJ in close proximity to the kidney. The sheath allows the urological procedure to be performed on the kidney or an associated organ by transporting the tools through the sheath to the area of concern. Additionally, the use of the sheath allows for the free flow and drainage of irrigant that is created during the procedure.

Currently, the access sheaths that are used in conjunction with urological procedures do not include any device or mechanism for containing or retaining the irrigant that exits the access sheath. Often this irrigant is spilled on the floor of the medical facility and is disposed of through the drainage system of the facility. The loss of particulate matter that may be entrained within the irrigant becomes a lost opportunity for examination and testing. The particulate matter could be beneficially analyzed after the procedure through procedures that are known in the art, to aid in the diagnosis of the patient or for broader testing and experimentation. What is needed is a way to collect the particulate matter created during percutaneous procedures.

BRIEF SUMMARY

A first representative embodiment provides an apparatus for collection of particulate matter during a surgical procedure. The apparatus includes an access sheath with a first end and a second end, and a first lumen through a length of the access sheath. A filter is connectable to the second end to receive flow from the second end of the access sheath.

An apparatus for the collection and retention of particulate matter during a surgical procedure is provided. The apparatus includes an access sheath with a first end capable of insertion into a patient during a medical procedure and a second end. A filter is connected to the access sheath to receive flow from the second end of the access sheath. A tube is provided that provides a flow path from the second end of the access sheath in conjunction with the filter.

A second representative embodiment provides a medical device. The medical device includes an elongate flexible access sheath with a first inserting end and a second end. A filter is removeably connected to the second end of the sheath to receive liquid therefrom, wherein the filter includes a mesh suitable for retaining particulate matter, but allowing liquid to pass through the mesh to exit the filter from an output end.

A third representative embodiment provides a method for performing surgical procedures. The method includes the first act of providing an access sheath with a first end and a second end and the second act of inserting the first end of the access sheath into a body passage of a patient and then directing the first end of the access sheath to a desired position within the patient. A filter is positioned downstream of the second end of the access sheath to receive flow from the second end of the access sheath.

Advantages of the present invention will become more apparent to those skilled in the art from the following description of the preferred embodiments of the invention that have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PREFERRED EMBODIMENTS

With reference to the figures, a system for collection and retention of particulate matter that is used with surgical procedures, specifically urological procedures, is provided. Generally, irrigant is used during urological procedures. Specifically, during percutaneous procedures on the kidney, such as percutaneous nephrolithotomy for staghorn or partial staghorn renal calculi, a significant amount of irrigant is used during the procedure, which may carry entrained particulate matter that is physically removed from the kidney. As is known to those of ordinary skill in the art, a sheath is often inserted through the urethral meatus to travel through the urethra, the bladder, and the ureter until it reaches the UPJ to provide a flow path for irrigant to exit the patient through their urinary tract. In addition to providing a flow path, the sheath is also beneficial because it provides a path for tools for use at the surgical zone, such as a laser fiber for breaking up calculi or a basket or retriever for removing fragments of the calculi. The use of the sheath enhances the ability for medical professionals to exchange tools because the sheath minimizes contact between the tools and the tissues of the patient.

Access sheaths 20 can be constructed using methods and materials that are known to those of ordinary skill in the art. Access sheaths are preferably flexible and kink-resistant. This allows for entry into a patient through an orifice and movement through a passageway within a patient. Access sheaths must be flexible enough to move throughout a desired passageway, and strong enough to maintain an open lumen through the sheath when the sheath is curved or bent during insertion. The steaths provide a relatively smooth outer surface to maximize ease of insertion and minimize discomfort for the patient. Specifically, commonly owned U.S. Pat. No. 5,380,304 and U.S. Pat. No. 5,700,253 disclose suitable structures for manufacturing flexible and kink resistant introducer or access sheaths, and the disclosure contained therein is hereby incorporated herein by reference in their entirety.

A first embodiment of an apparatus 10 for the collection and retention of particulate matter is provided as shown in FIGS. 1-4. The apparatus includes an access sheath 20, a skirt 28, a filter assembly 30, a tube 60, and a filter 40. The tube 60 provides a flow path for liquid from filter assembly 30, which is removeably attached to a proximal end 24 of the access sheath 20. Tube 60 can be connected to a container 80 so that the irrigant that flows through tube 60 can be saved, or alternatively, tube 60 can simply drain to the floor or a drainage system of the medical facility. Preferably, a filter 40 may be installed within filter assembly 30 and inserted into an aperture (not shown) formed at proximal end 24 of sheath 20. As irrigant flows through the access sheath 20, the irrigant is strained by the filter 40 to retain particulate matter within the filter 40.

The access sheath 20 is designed to be inserted through an orifice of the patient and run through a passageway to reach a specific area of the patient for a surgical procedure. Access sheath may be formed with a single lumen 26 that runs along the length of access sheath 20. In another embodiment shown in FIG. 5, an access sheath 120 may be formed with at least two lumens 126a, 126b that run along the length of the access sheath 120. Access sheaths that include multiple lumens are fully described in commonly assigned patent application Ser. No. 11/089,063 filed on Mar. 24, 2005, the disclosure of which is fully incorporated by reference herein. In embodiments that include at least two lumens, one of the lumens may be used as a drainage conduit for irrigant from the patient and another lumen may be used to provide a passageway for surgical tools through the access sheath to the surgical location for use in the medical procedure.

Figure 1:
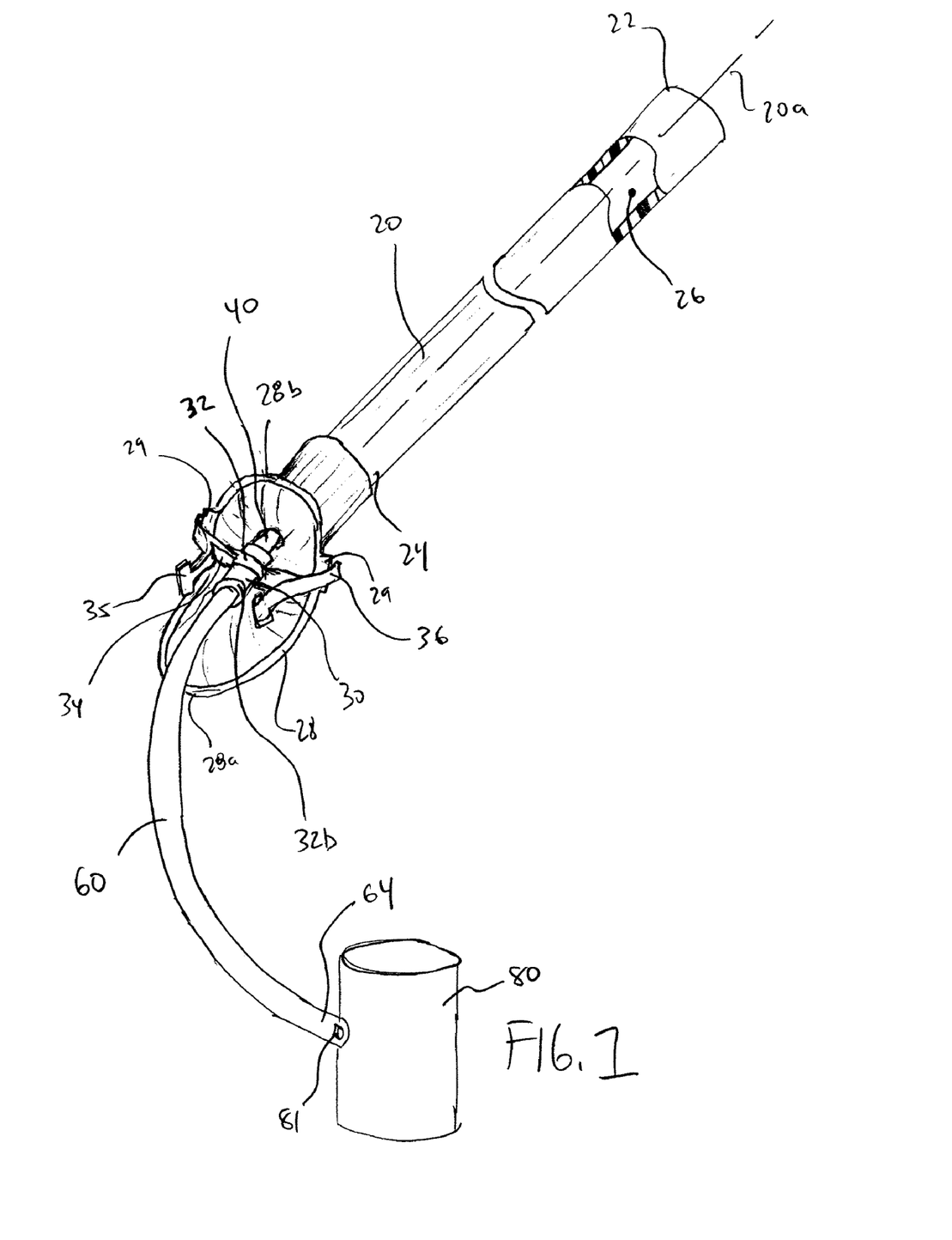
FIG. 1 is a perspective view of an embodiment of an apparatus for collection and retention of particulate matter.
Figure 2:
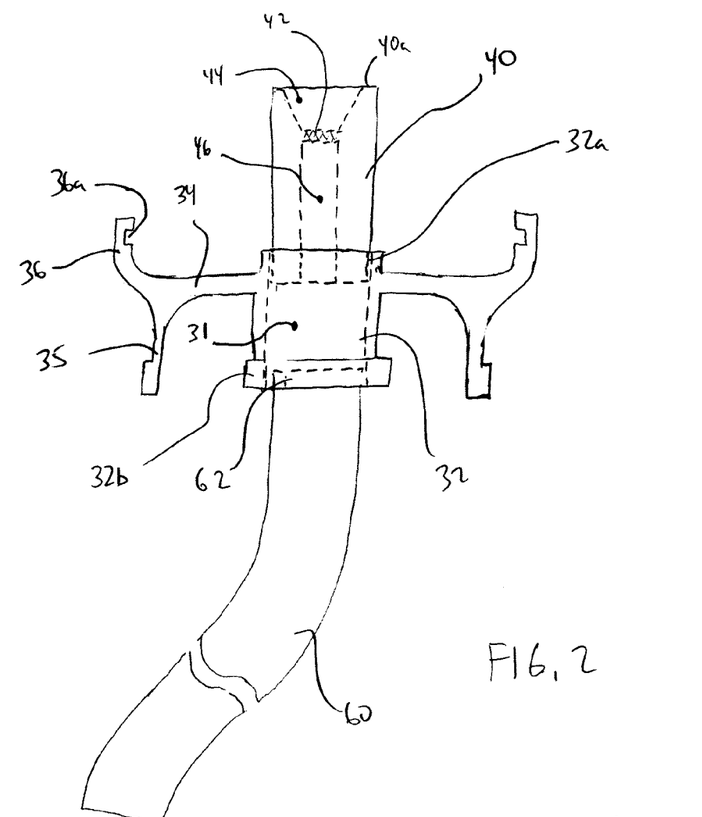
FIG. 2 is a partial cross-sectional view of the apparatus of FIG. 1.

The access sheath 20 includes a distal end 22 and a proximal end 24. As can be understood, both distal and proximal ends 22, 24 include apertures to allow for liquid to enter access sheath 20, flow through lumen 26, and exit the opposite end of access sheath 20. Proximal end 24 includes a skirt 28 that receives and supports filter assembly 30. Skirt 28 includes two flanges 29 that extend from opposite sides of the skirt 28. Flanges 29 provide a suitable structure for the hands 36 of the filter assembly 30 to engage to connect filter assembly 30 to the proximal end 24 of access sheath 20 when filter 40 is inserted into the aperture in proximal end 24.

When filter assembly 30 is connected to proximal end 24 of access sheath 20, filter 40 is inserted into an aperture in proximal end 24 of access sheath 20 to cause all liquid that enters access sheath 20 to flow through filter 40 within filter assembly 30.

Filter assembly 30 includes a holder 32 that is sized and shaped to retain filter 40 inserted within the distal end 32a of holder 32. Holder 32 includes a proximal end 32b that is sized to accept distal end 60a of tube 60 or similar structure. Holder 32 is formed with a lumen 31 to allow flow entering distal end 32a (that exits filter 40) to flow through holder 32 and out proximal end 32b. Filter assembly 30 additionally may include two or more arms 34 that extend in opposing directions radially from holder 32. Arms 34 each support a hand 36 and additionally may support a grip 35. Hand 36 is oriented approximately perpendicular from arm 34 and extends toward access sheath 20 when filter assembly 40 is engaged with access sheath 20. Each hand 36 preferably includes a notch 36a that accepts a flange 29 that extends from the skirt 28. Each arm 34 and corresponding hand 36 is positioned to engage one of the two flanges 29 that extend from the skirt 28. Specifically, when the hands 36 are not biased outward by the grips 35 (as discussed below) the tabs 29 are located within the respective notch 36a, and the filter assembly 30 is retained in connection with skirt 28 and the access sheath 20. Additionally, the connection between tab 29 and notch 36a sets the filter 40 (when inserted into holder 32) in the correct position such that distal end 42 of filter 40 is inserted into proximal end 24 of access sheath 20. Accordingly, in this position, substantially all irrigant and particulate matter that flows through access sheath 20 also flows through filter 40.

Each arm 34 additionally may include a grip 35 that extends perpendicularly from the arm 34 and in the opposite direction from the hand 36. Grips 35 are provided as the contact point to control the position of hands 36. Specifically, each of the two grips 35 may be compressed together, which rotates each of the two hands 36 about a pivot point located where arm 34, hand 36, and grip 35 meet. When grips 35 are compressed together hands 36 move outward away from contact with the respective tab 29.

Filter assembly 30 is preferably formed from a single molded piece. Filter assembly 30 should be flexible enough such that the two grips 35 can be positioned between opposing fingers of the user and pressed together but strong enough so that the inward biasing force of the opposite hands 36 is sufficient to retain filter assembly 30 on skirt 28 due to hands 36 contact with flanges 29. In some embodiments, filter assembly is manufactured from plastic. When the two grips 35 are pressed together, the two hands 36 are each rotated outward away from the flanges 29, which allows the filter assembly 30 to be removed from the access sheath 20. Filter assembly 30 should be flexible enough so that the movement of the grips 35 causes only elastic movement of the hands 36 so that the hands 36 and the grips 35 return to their original position when released.

Figure 3:
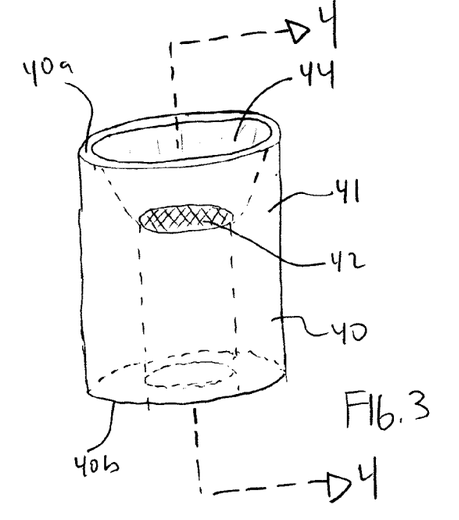
FIG. 3 is a perspective view of a filter of the apparatus of FIG. 1.
Figure 4:
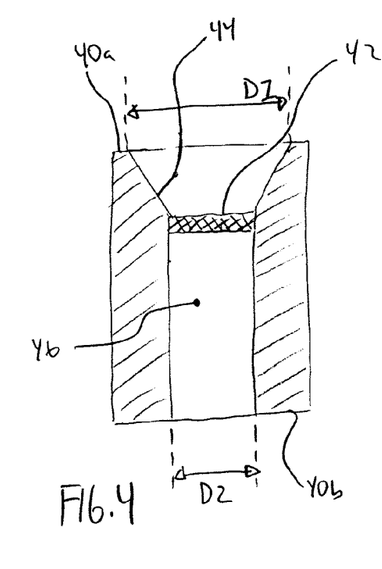
FIG. 4 is a cross-sectional view along line 4-4 FIG. 3.
Figure 8:
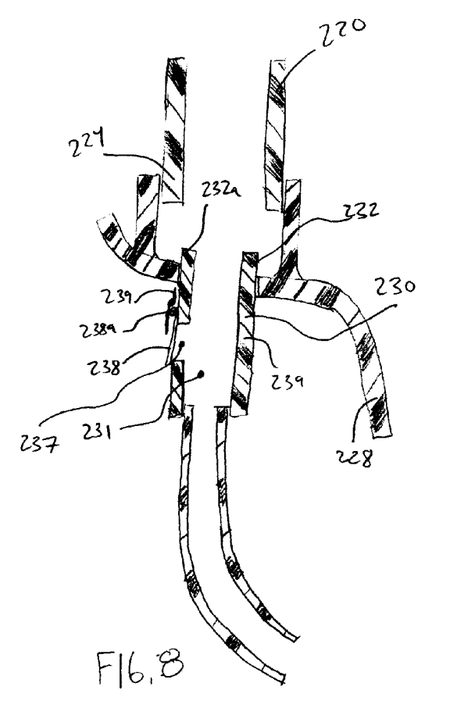
FIG. 8 is a partial cross-sectional view of the view of FIG. 6.

With reference to FIGS. 2-4, filter 40 is formed with a housing 41 and a mesh 41 located within housing 41. Filter 40 may be inserted into lumen 26 in proximal end 24 of access sheath 20 when filter assembly 30 is connected to skirt 28. Alternatively, in the embodiment shown in FIG. 8, filter 40 may be inserted into first lumen 138 on proximal end 136b of connector 136.

As shown in FIGS. 3 and 4, filter 40 is preferably includes a cylindrical outer surface 41 and an internal flow path, or lumen. Distal end 40a includes a lumen having a first diameter D1. Proximal end 40b includes a lumen having a second diameter D2. In some embodiments, D1 is the same length as D2. In other embodiments D1 is larger than D2. A mesh 42 is positioned within filter 40 such that substantially all liquid flow that enters filter 40 flows through mesh 42. Mesh 42 is preferably sized to allow liquid irrigant that enters the access sheath 20 to flow through the filter 40 without creating clogs or significantly retarding the mass flow rate of liquid that enters access sheath 20 from exiting filter 40. The mesh should be a small enough gauge to prevent particulate matter that is 0.5 mm in diameter or greater from flowing through 40. In some embodiments, mesh 42 may be formed from nylon. In other embodiments, mesh 42 may be formed from non water tight GORTEX®. In other embodiments mesh 42 may be formed from wire, polymers, or a nylon GORTEX® mixture. Mesh 42 may formed from other materials that are known to those of skill in the art to allow liquid flow therethrough but retain particulate matter.

As shown in FIG. 4, filter housing 41 is preferably formed with an inlet D1 larger than the diameter D2 of mesh 42. Additionally, filter 40 includes a tapered surface 44 connecting the inlet to the mesh area. This allows maximum room for tweezers or similar tools to remove the particulate matter that is collected on mesh 42.

A tube 60 is attached to the proximal end 32b of filter assembly 30. Tube 60 can be a conventional flexible tube, such as rubber or TYGON®, which includes a lumen 60a to allow flow through tube 60. In some embodiments, distal end 62 of tube 60 is inserted into aperture in proximal end of holder 32. Proximal end 64 of tube 60 may be connected to a container 80 by a suitable connector or nipple 81 to accept and retain liquid that flows through tube 60. Container 80 can be any conventional type of container known in the art to accept and retain liquids. Alternatively, container 80 can be a bag or similar flexible structure that can retain liquids. In other embodiments, proximal end 64 may not be connected to anything to allow the irrigant flowing within tube 60 to drain directly to the floor or other drainage system (not shown).

After the desired medical procedure is competed, filter assembly 30 may be removed from skirt 28 by biasing grips 35 together so that hands no longer engage tabs 29 that extend from skirt 28. Next, filter assembly 30 may be withdrawn from access sheath 20 and filter 40 may be removed from filter assembly 30. Any particulate matter can be removed from mesh 42 and analyzed using methods that are known to those of ordinary skill in the art. The filter 40 and filter assembly 30 can then be reconnected to skirt 28 for continued use, or the access sheath 20 can be removed from patient at the conclusion of the procedure.

Figure 5:
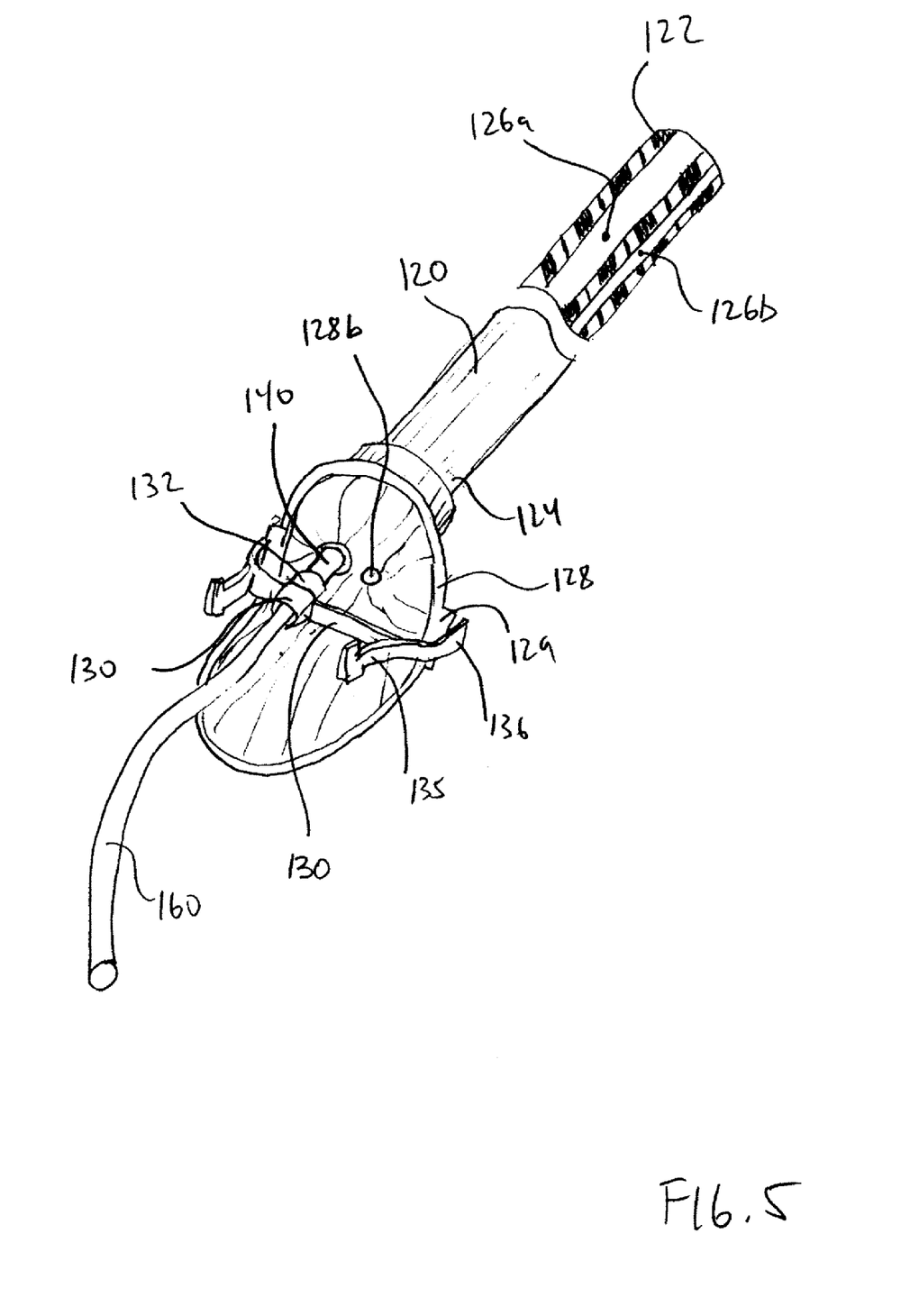
FIG. 5 is a perspective view of an alternate apparatus for collection and retention of particulate matter.

Turning now to FIG. 5, in embodiments where the access sheath 120 includes a first lumen 126a and a second lumen 126b, an alternate skirt 128 is engaged with proximal end 124 of access sheath 120. Specifically, skirt 128 includes a first aperture (not shown) that may receive filter 140 that extends from filter assembly 130. The first aperture provides an entrance into first lumen 126a. Skirt 128 additionally includes second aperture 128b that leads to the second lumen 126b of access sheath 120. As discussed above, second lumen 126b may be used for inserting and manipulating various external tools through access sheath 120 and out distal end 122 for use during the medical procedure.

Figure 11:
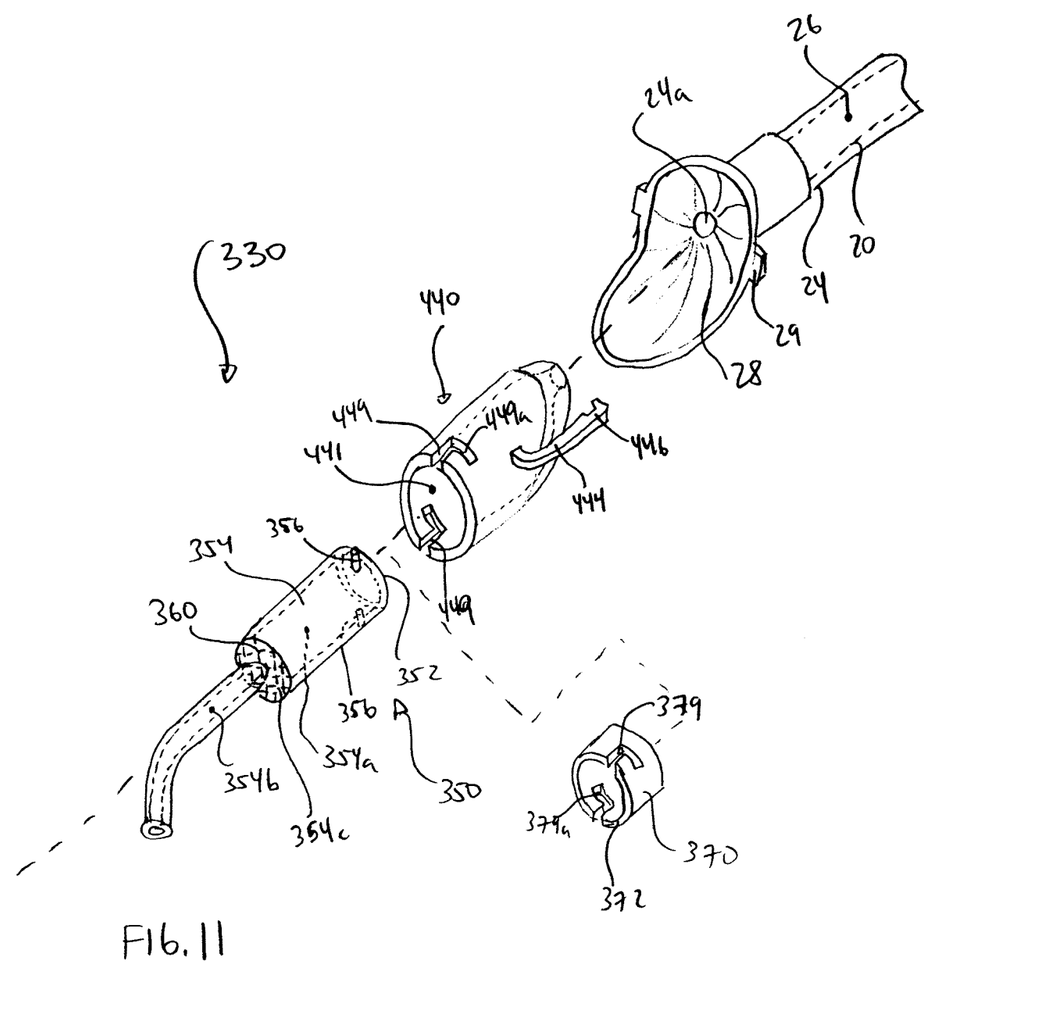
FIG. 11 is an exploded view of another embodiment of an apparatus for collection and retention of particulate matter.

The filter 140 is connected with the first aperture (not shown, but similar to aperture 24a of FIG. 11) in skirt 128 using a similar mechanism that is discussed in the embodiment above. Specifically, filter 140 is removeably retained by a filter assembly 130 that includes a holder 132 and a plurality of arms 134 that extend from holder 132 in opposite radial directions. Each arm includes a grip 135 and a hand 136 with a notch (not shown, but similar to notch 36a). As with the embodiment discussed above, the notches in hands 136 selectively engage tabs 129 that extend from skirt 128 to retain filter 140 inserted into aperture that extends into first lumen 126a in access sheath 120. Filter assembly 130 and filter 140 can be removed and returned to access sheath 120 by manipulating grips 135 as discussed above. In other embodiments, structure similar to the filter assembly 330 (discussed below) may be connectable with the first aperture of the skirt 128 and the tabs 129.

Turning now to FIGS. 11-17, an alternate filter assembly 330 is provided. Filter assembly 330 is connectable with proximal end 24 of access sheath 20 and includes an adaptor 340, a filter housing 350, and may include a cover 370 that is removeably attachable to filter housing 350 to retain particulate matter captured within filter housing 350.

Figure 14:
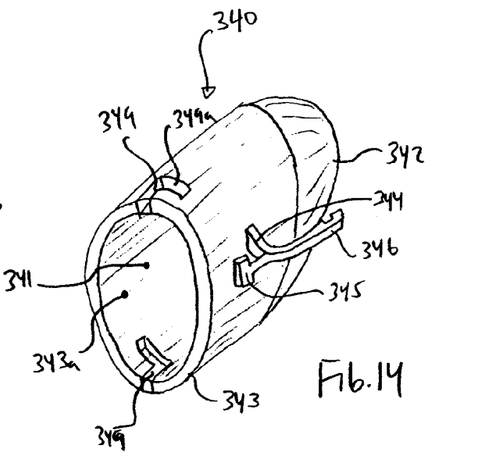
FIG. 14 is a perspective view of an alternate adaptor useable with the apparatus of FIG. 12.
Figure 15:
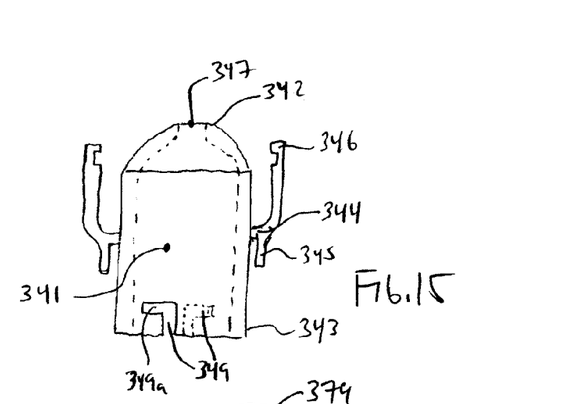
FIG. 15 is a plan view of the adaptor of FIG. 14.

As best shown in FIGS. 14-15, an adaptor 340 includes a distal end 342 that is connectable with proximal end 24 of sheath 20. In embodiments where proximal end 24 of sheath 20 includes skirt 28, distal end 342 of adaptor 340 is sized and shaped to engage skirt 28. Distal end 342 includes an aperture 347 that fluidly connects with proximal end 24 of sheath 20 to receive flow from an aperture 24a in proximal end 24 of sheath 20 to receive liquid that flows through lumen 26 of sheath 20. Similar to filter assembly 30 discussed above, adaptor 340 includes two or more arms 344 that extend radially from filter assembly 340. Each arm 344 supports a grip 345 and a hand 346 for connection with the flange 29 extending from skirt 28 on proximal end 24 of sheath 20. Arms, grips, and hands 344, 345, 346 are generally constructed and operate similarly to arms, grips, and hands 34, 35, 36 discussed above.

Each hand 346 may extend substantially perpendicularly from the respective arm 344 and is engageable with a corresponding flange 29 that extends radially from the skirt 28 to retain the adaptor 340 on the skirt 28. As discussed above with respect to previous filter assembly 30, grips 345 may extend from arms 344 and serve as the contact point for the user to control the position of the hands 346. Grips 345 may extend substantially perpendicularly from arms 344 in the opposite direction from hands 346, or may be oriented in another geometric configuration to allow for movement of hands 346 and a releasable connection with skirt 28.

The adaptor 340 forms a relatively tubular and hollow structure proximally of distal end 342. The adaptor 340 may form a lumen 341 that extends between the aperture 347 in the distal end 342 and an aperture 242a in a proximal end 343. Proximal end 343 may further include at least one slot 349 to receive a pin 356 or similar structure that extends from filter housing 350. The slot 349 may be dogleg or "L" shaped to allow pin 356 from the filter housing 350 (discussed below) to be selectively retained within the perpendicular portion 349a of slot 349. In some embodiments, adapter 340 includes two or more slots 349 that receive a similar number of pins 356 from filter housing 350. Slots 349 may be defined at consistent arc lengths from neighboring slots 349, or at other locations on proximal end 343 of adaptor 340.

Figure 12:
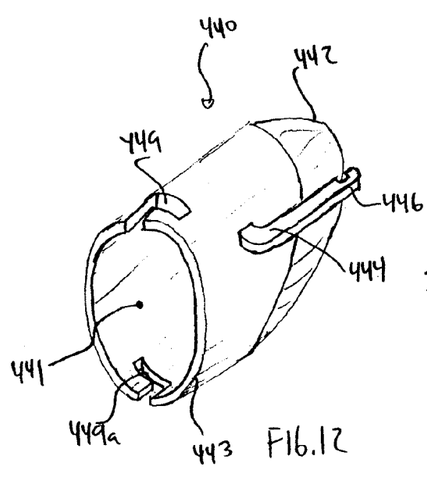
FIG. 12 is a perspective view of an adaptor of the apparatus of FIG. 11.
Figure 13:
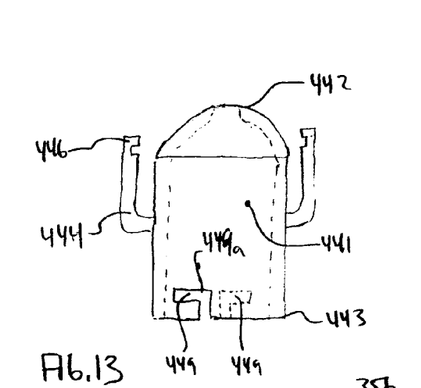
FIG. 13 is a plan view of the adaptor of FIG. 12.

Alternatively, as shown in FIGS. 12-13, an alternate adaptor 440 may be provided for engagement with skirt 28 and filter housing 350. Adaptor 440 is formed similarly to adaptor 340 with a lumen 441 between the distal and proximal ends 442, 443, and at least one slot 449 similar to the slot 349 discussed above. Distal end 442 is sized and shaped to engage skirt 28. An aperture 447 is defined on the distal end 442 to receive fluid from the lumen 26 of the sheath 30 that flows through an aperture 24a on the skirt 28. Adaptor 440 includes one or more arms 444 that extend from the outer surface of adaptor 440. In some embodiments, adaptor includes two or more arms 444. Arms 444 each include hands 446 or similar structures that are engageable with flange 29 extending from skirt 28 to removeably attach adaptor 440 to skirt 28 and sheath 20. Arms 444 are sufficiently flexible to be normally biased to engage hands 446 with flanges 29 in skirt 28, but sufficiently radially flexible to allow hands 446 to disengage flanges 29 to remove adaptor 440 from sheath 20.

Figure 16:
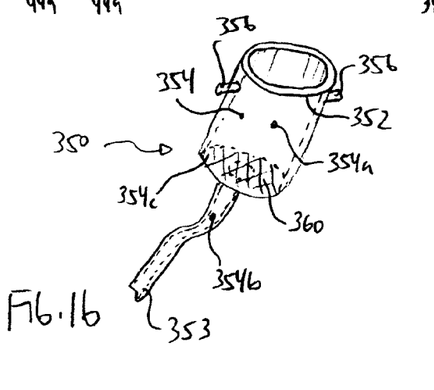
FIG. 16 is a perspective view of a filter housing of the apparatus of FIG. 11.

As best shown in FIG. 16, a filter housing 350 is sized and shaped to retain a filter mesh 360 installed therewithin and to be selectively connected with the proximal end 343 (443) of the adaptor 340 (440) or a cover 370. Filter housing 350 includes a distal end 352 and a proximal end 353. A filter 360 is provided within a lumen 354 within filter housing 350 between distal and proximal ends 352, 353. Lumen 354 may include a distal portion 354a that may have a larger diameter than a proximal portion 354b of lumen 354. Distal and proximal portions 354a, 354b may connect at a flat junction 354c, or lumen 354 may have a cross-section similar to lumen 46 of filter 40 as discussed below and best shown in FIG. 4. In embodiments with a flat junction 354c, filter 360 may be attached within distal portion 354a in contact with flat junction 354c. In embodiments shaped similarly to filter 40 of FIG. 4, filter mesh 360 may be provided at the base of the tapered surface within the distal lumen 354a.

Distal lumen 354a is selectively provided with a relatively large diameter or cross-section when compared to proximal lumen 354b to provide a large volume for collection of irrigant liquid before flowing through the proximal lumen 354b and filter mesh 360. The temporary collection of irrigant above filter mesh 360 allows particulate matter entrained within the irrigant some time for at least a portion of the particulate matter to settle out of solution and be deposited upon filter mesh 360, increasing the efficiency of the collection of the particulate matter within the filter housing 350. Further, as discussed below with reference to filter 40, the larger diameter of distal lumen 354a allows room for tweezers or similar tools to be extended therein to allow for removal of particulate matter from above filter mesh 360.

Figure 17:
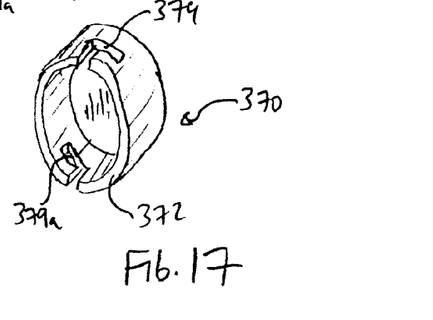
FIG. 17 is a perspective view of a cover of the apparatus of FIG. 11.

Distal end 352 of filter housing 350 includes two or more pins 356 that radially extend therefrom for removable connection with respective slots 349 (449) of the adaptor 340 (440) as discussed above. Specifically, the same number of pins 356 are provided as slots 349 (449) defined in the adaptor 340 (440) and slots 379 in the cover 370 (FIG. 17). Pins 356 are aligned at the same relative radial positions as the open ends of the slots 349 are defined on adaptor 340 (440) and can be inserted through open ends and then into perpendicular portions 349a of slots 349 to selectively retain filter housing 350 on adaptor 340 (440). Pins 356 are additionally provided to selectively engage slots 379 defined on an open end 372 of cover 370, when provided. Slots 379 are formed similarly to slots 349 and allow for cover 370 to be selectively retained on distal end 352 of filter housing 350, when the filter housing 350 is removed from the adaptor 340 (440). When installed, the cover 370 prevents particulate matter from exiting the distal end 352 of the filter housing 350.

Proximal lumen 354b may be defined within flexible tubing that extends from filter housing 350 below filter mesh 360 and flat junction 345c. Proximal lumen 354b provides a flow path for irrigant that flows through filter mesh 360 to flow from filter housing 350. Proximal lumen 354b may be connectable to a container 80 for collection of irrigant, or in other embodiments, proximal lumen may drain to the drainage system of the medical facility when it is not necessary to retain the irrigant for medical purposes.

Another alternate embodiment of an apparatus 200 for the collection and retention of irrigant is provided in FIGS. 6-9. The apparatus 200 includes an access sheath 220 with a skirt 228, a filter assembly 230, a removable filter 240, and a tube 260. In some embodiments, skirt 228 may be integral with access sheath 220 and partially surround the connection between access sheath 220, filter 240, and filter assembly 230. Filter 240 may be installed within an aperture 237 in filter assembly 230 so that filter 240 can be removed from apparatus 200 without disconnecting filter assembly 230 and tube 260 from access sheath 220.

Figure 6:
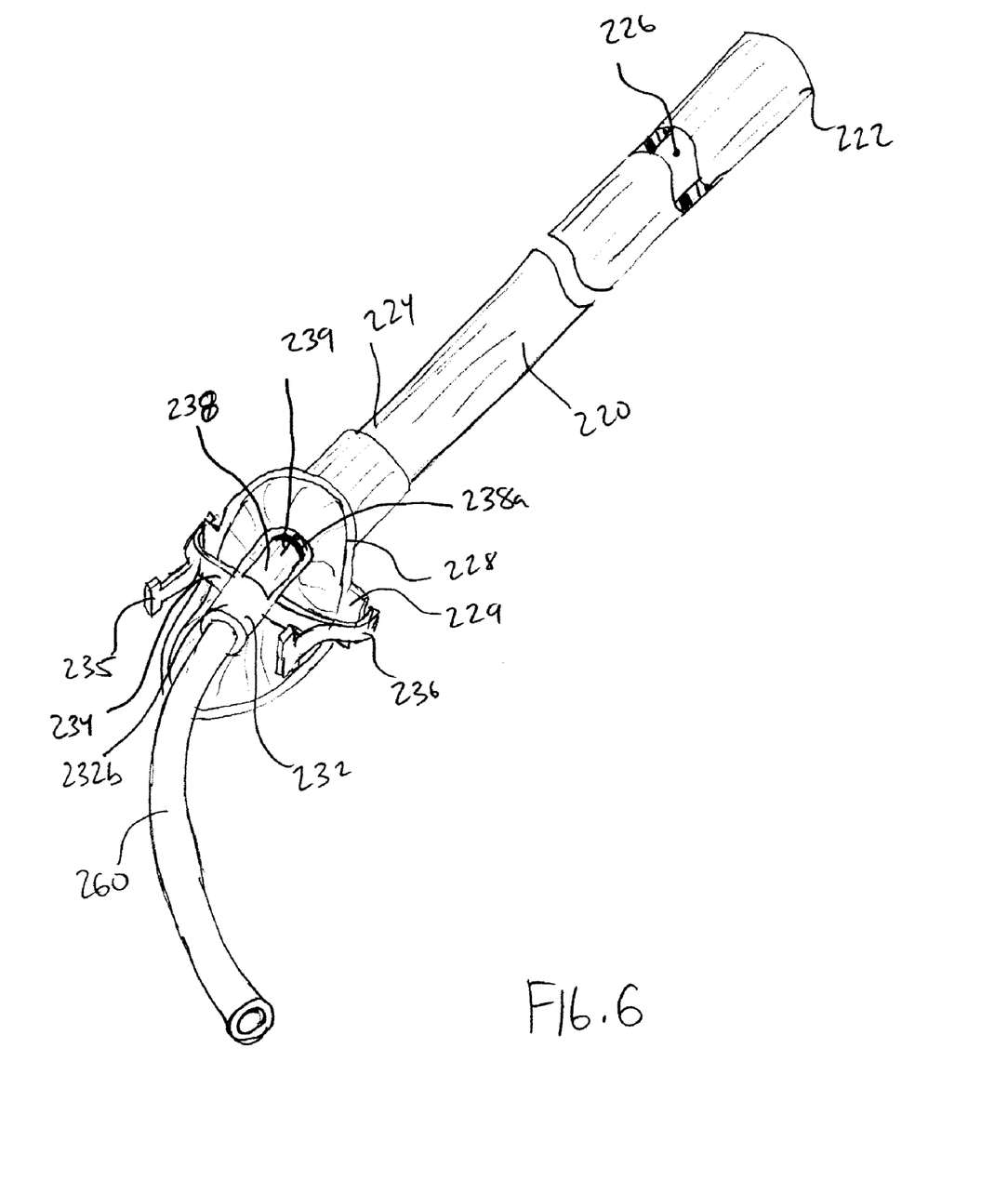
FIG. 6 is perspective view of another embodiment of an apparatus for collection and retention of particulate matter with a filter not installed.
Figure 7:
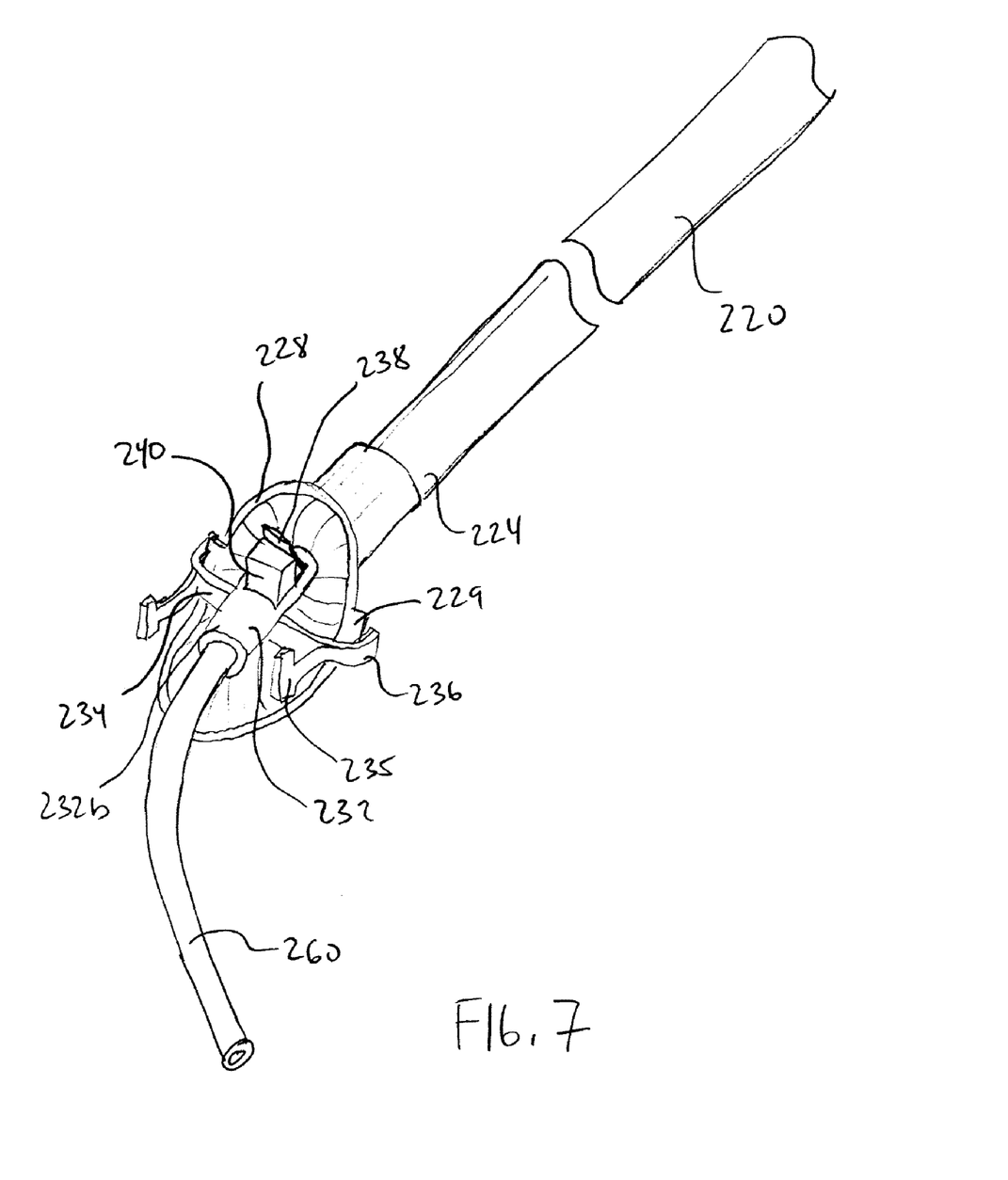
FIG. 7 is the view of FIG. 6 with a filter installed.

Filter assembly 230 includes a holder 232, a pair of arms 234 that extend from holder in opposite directions, and each arm 234 connects with a hand 236 with a notch (not shown) and may include a grip 235. Filter assembly 230 is removeably connectable with skirt 228 with the notches (not shown) of hands 236 engaging tabs 229 that extend from skirt 228 in the same manner as in the previous embodiments discussed above.

Access sheath 220 includes a distal end 222 and a proximal end 224 and a lumen 226 that extends through the length of access sheath 220. Access sheath 220 is constructed in a similar manner as the embodiments discussed above.

Filter assembly 230 includes an aperture 237 formed along a section of a surface of housing 232. Aperture 237 is preferably located near a distal end 232a of filter assembly 230. Filter assembly 230 may additionally include a cover 238 that is mounted to filter assembly 230 in the vicinity of aperture 237 to normally substantially enclose aperture 237 to prevent irrigant flowing through filter assembly 230 to escape through aperture 237. As shown in FIGS. 6-9, cover 238 may be attached to filter assembly 230 at a seam 238a and be biased toward filter assembly 230 by a spring 239 or other similar connection to maintain cover 238 enclosing aperture 237.

Figure 9:
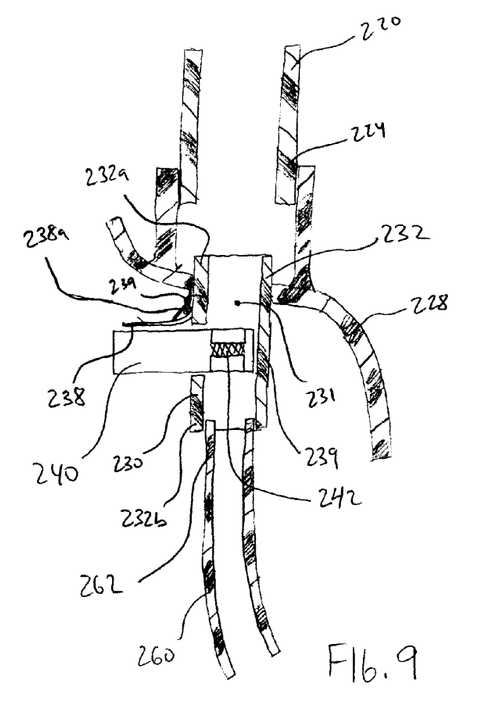
FIG. 9 is a partial cross-sectional view of the view of FIG. 7.

As shown in FIGS. 7 and 9, a filter 240 may be inserted through aperture 237 to extend through lumen 231 in filter assembly 230 and seal against the closed side 239 of filter assembly 230. In embodiments that include cover 238, filter 240 is insertable into aperture 237 in filter assembly 230 by pulling cover 238 away from aperture 237 against the biasing force of spring 239 (where provided). When installed, a handle 244 of filter 240 extends outward from filter assembly 230 and can be manipulated to remove filter 240 from filter assembly 230 without disconnecting filter assembly 230 from skirt 228 or the other components of the assembly. Filter 240 includes a mesh 242 that is formed similarly to mesh 42 discussed above.

In some embodiments, filter 240 may be provided with an inlet diameter (not shown) that is greater than the mesh 242 and outlet diameters (not shown). In these embodiments, filter 240 includes a tapered surface (not shown) connecting the inlet to the mesh area 242, as discussed and shown in FIG. 4 in conjunction with the embodiment discussed above.

Figure 10:
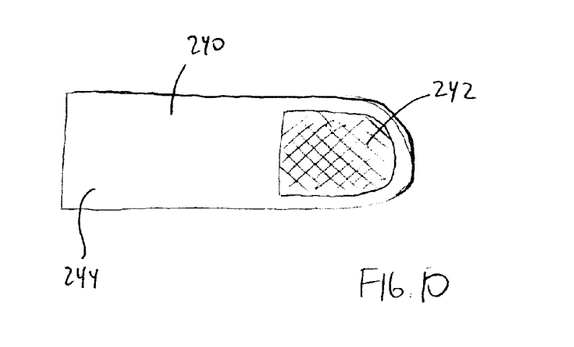
FIG. 10 is a top view of the filter of FIG. 7.

FIG. 10 provides a top partial cross-sectional view of filter 240 inserted through aperture 237 of tube 260. As can be understood, although filter 240 is not as wide as lumen 231 of filter assembly, filter 240 encloses the majority of the internal area of lumen 231. Accordingly, when filter 240 is fully inserted into filter assembly 230 a majority of irrigant that enters access sheath 220 flows through mesh 242 in filter. Accordingly, filter 240 retains substantially all, or a large percentage of, particulate matter that may be entrained with the irrigant.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. An apparatus for collection and retention of particulate matter during a surgical procedure comprising:
   (a) an access sheath with a first end and a second end, and a first lumen through a length of the access sheath, further comprising a skirt disposed upon the second end and a plurality of flanges that radially extend from the skirt;
   (b) a filter assembly removably connectable to the second end to receive flow from the second end of the access sheath, the filter assembly comprising an adaptor, a filter housing, and a filter mesh disposed within the filter housing, wherein adaptor and filter housing are removeably connectable with each other such that the filter housing is fluidly connected with the first lumen when the filter assembly is connected to the second end of the access sheath,
   the adaptor is configured with a plurality of arms that extend radially from a side surface of the adaptor, the arms each comprise a hand that is configured to engage a respective flange upon the skirt, the arms each being biased inward such that the adaptor is mechanically fixed to the skirt when the hands engage the respective flange;
   the filter housing is a hollow cylindrical member with the filter mesh disposed within a flow path through the filter housing.

2. The apparatus of claim 1 wherein the filter housing includes an aperture that allows for insertion and removal of the filter mesh with respect to the filter housing when the filter assembly is connected to the second end of the access sheath.

3. The apparatus of claim 2 wherein the filter housing includes a cover that substantially encloses the aperture when the filter mesh is not inserted into the aperture.

4. The apparatus of claim 1 wherein the filter mesh is configured to retain particulate matter but allow liquid to flow therethrough.

5. The apparatus of claim 4 wherein the filter mesh is sized to retain particulate matter that is at least 0.5 mm in diameter.

6. The apparatus of claim 1, wherein the skirt comprises an arcuate generally concave profile, and a distal portion of the adaptor comprises an arcuate and generally convex profile substantially opposite the concave profile of the skirt, wherein the distal end of the adaptor is configured to make surface to surface contact with the skirt.

7. The apparatus of claim 1, wherein the adaptor and filter housing are removeably connectable with one or more slots disposed upon a proximal portion of the adaptor that are configured to receive one or more pins extending radially from a distal portion of the filter housing.

8. The apparatus of claim 1, wherein the filter housing is fluidly connected to an elongate tube that receives fluid flowing through the filter mesh such that fluid may be routed to a remote location from the proximal end of the access sheath.

9. The apparatus of claim 1, wherein the access sheath includes a first lumen for irrigant flow from the first end of the access sheath through the second end and a parallel second lumen, wherein the filter assembly is in fluid communication with the first lumen.

10. A method of performing surgical procedures comprising the acts of:
    (a) providing an access sheath with a first end and a second end with a skirt comprising a plurality of flanges disposed upon the second end;
    (b) inserting the first end of the access sheath into a body passage of a patient and directing the first end of the access sheath to a desired position within the patient; and
    (c) positioning and fixing a filter assembly downstream of the second end of the access sheath to receive flow from the second end of the access sheath, wherein the filter assembly comprises an adaptor, a filter housing, and a filter mesh disposed within the filter housing, and the adaptor and filter housing are removeably connectable with each other such that the filter housing is fluidly connected with a lumen through the access sheath,
    wherein the adaptor is configured with a plurality of arms that extend radially from a side surface of the adaptor, each arm comprises a hand that is configured to engage a respective flange upon the skirt, the arms each being biased inward such that the adaptor is mechanically fixed to the skirt when the hands engage the respective flange,
    wherein the filter housing is a hollow cylindrical member with the filter mesh disposed within a flow path through the filter housing.

11. The method of claim 10 wherein the access sheath includes a first lumen to allow for liquid flow from the first end to the second end and a parallel second lumen, wherein the filter assembly receives flow from the first lumen.

12. The method of claim 10 wherein the filter mesh is removeably insertable into the filter housing when the filter assembly is operatively engaged with the second end of the access sheath.

13. The method of claim 12 wherein the filter mesh is removable from the filter housing while the filter assembly remains operatively engaged with the access sheath.

* * * * *